(12) United States Patent
Bauer et al.

(10) Patent No.: US 6,642,294 B1
(45) Date of Patent: Nov. 4, 2003

(54) MIXTURES WITH SPECIAL SOFTENING AGENTS SUITED AS A SOLID ELECTROLYTE OR SEPARATOR FOR ELECTROCHEMICAL CELLS

(75) Inventors: Stephan Bauer, Hochdorf-Assenheim (DE); Bernd Bronstert, Otterstadt (DE); Helmut Möhwald, Annweiler (DE); Hans-Josef Sterzel, Dannstadt-Schauernheim (DE); Werner Hesse, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/509,690

(22) PCT Filed: Oct. 1, 1998

(86) PCT No.: PCT/EP98/06238
§ 371 (c)(1),
(2), (4) Date: Jul. 17, 2000

(87) PCT Pub. No.: WO99/18621
PCT Pub. Date: Apr. 15, 1999

(30) Foreign Application Priority Data

Oct. 2, 1997 (DE) .................................... 197 43 748
Oct. 9, 1997 (DE) .................................... 197 44 659
Apr. 13, 1999 (DE) .................................... 199 16 562

(51) Int. Cl.$^7$ .................................................. C08K 3/18

(52) U.S. Cl. .................. 524/430; 524/401; 524/404; 524/414; 524/415; 524/428

(58) Field of Search ............................. 524/430, 404, 524/401, 414, 415, 428

(56) References Cited

U.S. PATENT DOCUMENTS

| 4,129,543 A | * | 12/1978 | Kaplan | 260/29.15 |
| 4,183,843 A | * | 1/1980 | Koenig | 260/40 |
| 5,011,751 A | | 4/1991 | Yoneyama et al. | 429/192 |
| 5,047,308 A | * | 9/1991 | Usami | 430/138 |
| 5,108,832 A | * | 4/1992 | Nugent | 428/304.4 |
| 5,279,910 A | | 1/1994 | Sasaki et al. | 429/213 |

(List continued on next page.)

FOREIGN PATENT DOCUMENTS

| DE | 44 31 773 A1 | 3/1995 |
| EP | 0 537 930 A1 | 4/1993 |
| EP | 557 250 A1 | 8/1993 |
| EP | 0 559 317 A1 | 9/1993 |
| EP | 0 576 686 A1 | 1/1994 |
| EP | 0 585 072 A1 | 3/1994 |
| EP | 0 599 534 B1 | 6/1994 |

(List continued on next page.)

OTHER PUBLICATIONS

Ullman's Batteries Encyclopedia of Industrial Chemistry, 5th Ed., vol A3, p. 343–397 No date available.
Zhang et al. "A Novel Electrolyte Solvent for Rechargeable Lithium and Lithium–Ion Batteries" Journal of Electrochem. Soc. vol. 143, No. 12 (12/96) pp. 4047–4053.

*Primary Examiner*—Edward J. Cain
(74) *Attorney, Agent, or Firm*—Keil & Weinkauf

(57) ABSTRACT

A mixture Ia comprises a mix IIa composed of
  a) from 1 to 95% by weight of a solid III, preferably a basic solid III, with a primary particle size of from 5 nm to 20 μm and
  b) from 5 to 99% by weight of a polymeric composition IV, obtainable by polymerizing
  b1) from 5 to 100% by weight, based on the composition IV, of a condensation product V of
    α) at least one compound VI which is capable of reacting with a carboxylic acid or with a sulfonic acid or with a derivative or a iixture of two or more of these, and
    β) at least 1 mol per mole of the compound VI of a carboxylic acid or sulfonic acid VII which has at least one functional group capable of free-radical polymerization, or of a derivative thereof or of a mixture of two or more thereof and
  b2) from 0 to 95% by weight, based on the composition IV, of another compound VIII with an average molecular weight (number average) of at least 5000 having polyether segments in its main or side chain and at least one ester of the formula (E1) to (E5)

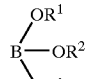

(E1)

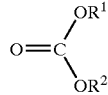

(E2)

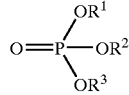

(E3)

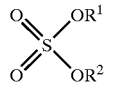

(E4)

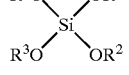

(E5)

where each of $R^1$, $R^2$, $R^3$ and $R^4$ is identical with or different from the others and, independently of the others, is linear or branched-chain $C_1$–$C_4$-alkyl (—$CH_2$—$CH_2$—O)$_n$—$CH_3$, where n is from 1 to 3, $C_3$–$C_6$-cycloalkyl or an aromatic hydrocarbon group which may in turn be substituted, with the proviso that at least one of the groups $R^1$, $R^2$, $R^3$ or $R^4$ is (—$CH_2$—$CH_2$—O)$_n$—$CH_3$, where n is from 1 to 3.

18 Claims, No Drawings

U.S. PATENT DOCUMENTS 5,674,437 A * 10/1997 Geisel .................... 264/21
5,681,669 A    10/1997 Yoshio et al. ............ 429/194
6,258,471 B1 *  7/2001 James .................... 428/694

FOREIGN PATENT DOCUMENTS

| | | |
|---|---|---|
| EP | 0 696 077 A2 | 2/1996 |
| EP | 0 698 933 A1 | 2/1996 |
| JP | 58 206 078 | 12/1983 |
| JP | 61 256 573 | 11/1986 |
| JP | 07 161 357 | 6/1995 |
| JP | 09 115 548 | 5/1997 |
| WO | WO 94/24715 | 10/1994 |
| WO | WO 97/16862 | 5/1997 |

* cited by examiner

MIXTURES WITH SPECIAL SOFTENING AGENTS SUITED AS A SOLID ELECTROLYTE OR SEPARATOR FOR ELECTROCHEMICAL CELLS

The present invention relates to mixtures which, inter alia, are suitable for electrochemical cells with electrolytes containing lithium ions; the use of these, e.g. in solid electrolytes, separators and electrodes; solid electrolytes, separators, electrodes, sensors, electrochromic windows, displays, capacitors and ion-conducting films which comprise a mixture of this type; electrochemical cells with such solid electrolytes, separators and/or electrodes; and also the use in electrochemical cells of the solids present in the mixtures, for improving cycle stability.

Electrochemical cells, in particular those which are rechargeable, are well known, for example from Ullmann's Encyclopedia of Industrial Chemistry, 5th ed., Vol. A3, VCH Verlagsgesellschaft mbH, Weinheim, 1985, pages 343–397.

Due to their high specific energy storage density, lithium batteries and lithium ion batteries occupy a particular position among these cells, especially as secondary cells.

As described, inter alia, in the above extract from "Ullmann", the cathodes of such cells contain lithiated compound oxides of manganese, cobalt, vanadium or nickel; these may be described in the stoichiometrically simplest case as $LiMn_2O_4$, $LiCoO_2$, $LiV_2O_5$ or $LiNiO_2$.

These compound oxides react reversibly with substances, such as graphite, which are capable of incorporating lithium ions into their lattice, the lithium ions being removed from the crystal lattice and the metal ions within this, such as manganese, cobalt or nickel ions, being oxidized. In an electrochemical cell this reaction can be used to store electrical energy by separating the compound accepting lithium ions, i.e. the anode material, from the lithium-containing compound oxide, i.e. the cathode material, by means of an electrolyte through which the lithium ions from the compound oxide can migrate into the anode material (charging).

The compounds suitable for reversible storage of lithium ions are usually secured to collector electrodes by means of a binder.

During charging of the cell, electrons flow through an external voltage source and lithium cations through the electrolyte toward the anode material. When the cell is used, the lithium cations flow through the electrolyte, but the electrons flow from the anode material to the cathode material through a load.

In order to avoid a short circuit within the electrochemical cell, a layer which is electrically insulating but permeable co lithium cations is located between the two electrodes. This may be what is known as a solid electrolyte or a conventional separator.

As is well known, solid electrolytes and separators are composed of a carrier material, incorporated into which are a dissociable compound which contains lithium cations and serves to increase lithium-ion conductivity, and also usually other additives, such as solvents.

Solid electrolytes based on polyalkylene oxides are known, and are described, for example, in EP-A 559 317, EP-A 576 686, EP-A 537 930, EP-A 585 072 and U.S. Pat. No. 5,279,910. The polyethers described in these references are modified at their end groups or functional groups, for example by means of (meth)acryloyl groups, and are crosslinked by introducing energy (heat or light) before they are used as solid electrolyte. They generally also contain a conducting salt, e.g. $LiPF_6$, to improve their conductivity.

The use of a solid to improve the mechanical, thermal and electrical strength of the solid electrolyte is not described in these references. Accordingly, and in spite of crosslinking, the systems described in these references do not always have satisfactory properties with regard to mechanical strength and the porosity of the resultant films, and short-circuit protection.

The solvents used hitherto in Li storage batteries have been predominantly alkyl ethers, such as dimethyl ether, and alkene carbonates, such as ethylene carbonate (EC) and propylene carbonate (PC). Such systems are described, inter alia, in JP 08 273 700 and JP 09 115 548.

Electrolyte solutions based on various esters are also known.

For example, WO97/16862 describes an electrolyte solution which comprises borates of the following formulae (A) to (D):

(A)

(B)

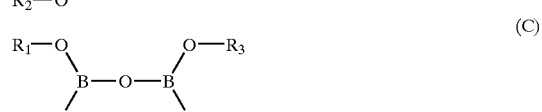

(C)

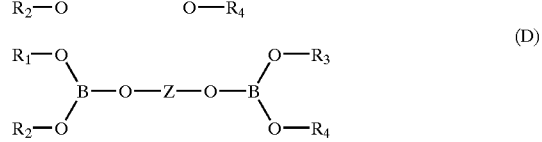

(D)

where X is halogen, $R^1$, $R^2$, $R^3$ and $R^4$ are straight-chain or branched-chain aliphatic or aromatic alkyl which may be substituted with substituents of various electronegativities, and Z is a straight-chain or branched-chain aliphatic or aromatic alkyl or siloxane group.

J. Electrochem. Soc., 143, 1996 pp. 4047–4053 describes an electrolyte solvent for rechargeable lithium and lithium-ion batteries based on a borate termed BEG-1 and having the formula (E) below, combined with EC and/or PC.

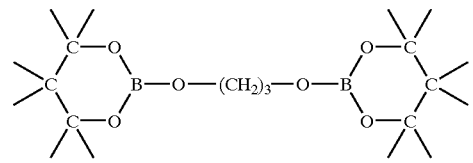

EP-B-0 599 534 describes carbonate compounds of the following formula (F)

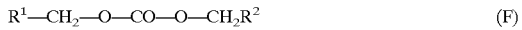

$R^1—CH_2—O—CO—O—CH_2R^2$ (F)

where $R^1$ is hydrogen, alkyl or alkyl substituted with one or more halogen atoms, and $R^2$ is allkyl with no hydrogen in the α position or alkyl with no hydrogen in the α position and substituted with one or more halogen atoms, with the proviso that $R^1$ is not identical with $R^2$, excluding the compound $C_2H_5—O—CO—O—CH_2—(CF_2)_4—H$ and also its use in a non-aqueous electrolyte solution.

EP-A 0 698 933 relates to a non-aqueous secondary cell which encompasses a specific eletrolyte solution including, inter alia, phosphoric triesters of the formula RO)$_3$P=O, where each of the groups R is identical or different and is C$_1$–C$_6$-alkyl or two RO groups may form a ring, together with the phosphorus atom to which they are bonded. Alkyl phosphates of this type and their use in non-aqueous electrolyte solutions and in secondary cells are likewise described in EP-A 0 696 077.

The use of phosphates of the formula O=P(—O—(CH$_2$CH$_2$O)$_q$R$^2$)$_3$, where n and q are from 1 to 10 and R$^2$ is C$_1$–C$_4$-alkyl, as electrolyte in zinc batteries is described in JP 07 161 357.

Other phosphates having hydrocarbon groups, and also the use of these as electrolyte in lithium ion batteries, are described in JP 58 206 078.

JP 61 256 573 describes an electrolyte based on a polymer of a phosphate containing at least one polymerizable group.

It is an object of the present invention to overcome the disadvantages described and to provide a mixture which is suitable in particular for producing solid electrolytes and separators, but can also be used for producing electrodes in electrochemical cells and for other applications described herein.

We have found that this object is achieved by means of the novel mixture in which a solid III as defined below is present; the use of the novel mixture gives solid electrolytes, separators or electrodes which, in comparison with the systems known hitherto, have improved short-circuit protection, increased compressive strength, in particular at above 120° C., and also greater porosity. and are moreover capable of sustained suppression of Li dendrite formation. The presence of the solid also provides electrochemical cells with improved cycle stability and higher current capacities. If the preferred basic solids are used, the acid formed during operation of an electrochemical cell is moreover scavenged or neutralized.

By using the esters present in the mixture and having the formulae (E1) to (E5) as defined herein, the mechanical properties of the films produced from the mixture and also the ease with which they can be peeled from temporary carriers are improved.

At the same time, the esters used also have electrolyte properties.

One embodiment of the present invention therefore provides a mixture Ia, comprising a mix IIa composed of a) from 1 to 95% by weight of a solid III, preferably a basic solid III, with a primary particle size of from 5 nm to 20 μm and b) from 5 to 99% by weight of a polymeric composition IV, obtainable by polymerizing b1) from 5 to 100% by weight, based on the composition IV, of a condensation product V of α) at least one compound VI which is capable of reacting with a carboxylic acid or with a sulfonic acid or with a derivative or a mixture of two or more of these, and β) at least 1 mol per mole of the compound VI of a carboxylic acid or sulfonic acid VII which has at least one functional group capable of free-radical polymerization, or of a derivative thereof or of a mixture of two or more thereof and b2) from 0 to 95% by weight, based on the composition IV, of another compound VIII with an average molecular weight (number average) of at least 5000 having polyether segments in its main or side chain and at least one ester of the formula (E1) to (E5)

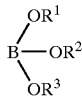
(E1)

(E2)

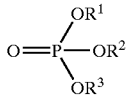
(E3)

(E4)

(E5)

where each of R$^1$, R$^2$, R$^3$ and R$^4$ is identical with or different from the others and, independently of the others, is linear or branched-chain C$_1$–C$_4$-alkyl, (—CH$_2$—CH$_2$—O)$_n$—CH$_3$, where n is from 1 to 3, C$_3$–C$_6$-cycloalkyl or an aromatic hydrocarbon group, which may in turn be substituted, with the proviso that at least one of the groups R$^1$, R$^2$, R$^3$ or R$^4$ is (—CH$_2$—CH$_2$—O)$_n$—CH$_3$, where n is from 1 to 3.

The above mixture Ia preferably comprises a mix IIa composed of a) from 1 to 95% by weight of a solid III, preferably a basic solid III, with a primary particle size of from 5 nm to 20 μm and b) from 5 to 99% by weight of a polymeric composition IV, obtainable by polymerizing b1) from 5 to 100% by weight, based on the composition IV, of a condensation product V of α) a polyhydric alcohol VI containing carbon and oxygen in its main chain and β) at least 1 mol per mole of the polyhydric alcohol VI of an α,β-unsaturated carboxylic acid VII and b2) from 0 to 95% by weight, based on the composition IV, of another compound VIII with an average molecular weight (number average) of at least 5000, having polyether segments in its main or side chain.

In another embodiment, the present invention provides a mixture Ib, comprising a mix IIb composed of a) from 1 to 95% by weight of a solid III, preferably a basic solid, with a primary particle size of from 5 nm to 20 μm and b) from 5 to 99% by weight of a polymer IX, obtainable by polymerizing b1) from 5 to 75% by weight, based on the polymer IX, of a compound X capable of free-radical polymerization and differing from the carboxylic acid or the sulfonic acid VII or from a derivative thereof, or of a mixture of two or more thereof and b2) from 25 to 95% by weight, based on the polymer IX, of another compound VIII with an average molecular weight (number average) of at least 5000, having polyether segments in its main or side chain, and at least one ester of the formula (E1) to (5)

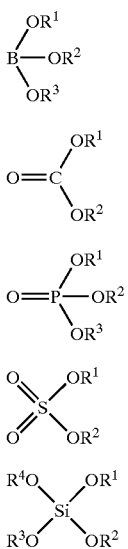

(E1), (E2), (E3), (E4), (E5)

where each of $R^1$, $R^2$, $R^3$ and $R^4$ is identical with or different from the others and, independently of the others, is linear or branched-chain $C_1$–$C_4$-alkyl, $(-CH_2-CH_2-O)_n-CH_3$, where n is from 1 to 3, $C_3$–$C_6$-cycloalkyl or an aromatic hydrocarbon group, which may in turn be substituted, with the proviso that at least one of the groups $R^1$, $R^2$, $R^3$ or $R^4$ is $(-CH_2-CH_2-O)_n-CH_3$, where n is from 1 to 3.

The solids III used are mainly inorganic solids, preferably inorganic basic solids selected from the class consisting of oxides, compound oxides, silicates, sulfates, carbonates, phosphates, nitrides, amides, imides and carbides of the elements of the 1st, 2nd, 3rd or 4th main group or the 4th subgroup of the periodic table; a polymer selected from the class consisting of polyethylene, polypropylene, polystyrene, polytetrafluoroethylene, polyvinylidene fluoride, polyamides and polyimides; a solid dispersion comprising a polymer of this type; or a mixture of two or more of these.

Particular examples are: oxides, such as silica, calcium oxide, alumina, magnesium oxide and titanium dioxide, compound oxides, for example of the elements silicon, calcium, aluminum, magnesium and titanium; silicates, such as ladder-type silicates, ino-, phyllo- and tectosilicates, preferably wollastonite, in particular hydrophobicized wollastonite; sulfates, such as those of alkali metals and alkaline-earth metals; carbonates, for example those of alkali metals and alkaline-earth metals, for example calcium, magnesium, barium, lithium, polassium or sodium carbonate; phosphates, such as apatites; nitrides; amides; imides; carbides; polymers, such as polyethylene, polypropylene, polystyrene, polytetrafluoroethylene and polyvinylidene fluoride: polyamides; polyinides; and other thermoplastics, thermosets and microgels, and solid dispersions, in particular those which comprise the polymers mentioned above, and also mixtures of two or more of the abovementioned solids.

According to the invention, the solids III preferably used are inorganic Li-ion-conducting solids, more preferably an inorganic basic Li-ion-conducting solid.

Particular mention may also be made of: lithium borates, such as $Li_4B_6O_{11}* xH_2O$ . $Li_3(BO_2)_3$, $Li_2B_4O_7*xH_2O$, $LiBO_2$, where x can be a number from 0 to 20; lithium aluminates, such as $Li_2O * Al_2O_3*H_2O$, $LiAl_2O_4$, $LiAlO_2$; lithium aluminosilicates, such as lithium-containing zeolites, feldspars, feldspathoids, phyllo- and inosilicates, and in particular $LiAlSi_2O_6$ (spodumene), $LiAlSi_4O_{10}$ (petullite), $LiAlSiO_4$ (eucryptite), micas, such as $K[Li,Al]_3$ $[AlSi]_4O_{10}(F-OH)_2$,/$K[Li,Al,Fe]_3$ $[AlSi]_4O_{10}(F-OH)_2$; lithium zeolites, in particular those whose form is fiber-like, sheet-like or cube-like, in particular those of the formula $Li_{2/z}O*Al_2O_3*xSiO_2*yH_2O$ where z is valence-related, x is from 1.8 to about 12 and y is from 0 to about 8; lithium carbides, such as $Li_2C_2$, $Li_4C$; $Li_3N$; lithium oxides and compound lithium oxides, such as $LiAlO_2$, $Li_2MnO_3$, $Li_2O$, $Li_2O_2$, $Li_2MnO_4$, $Li_2TiO_3$; $Li_2NH$; $LiNH_2$; lithium phosphates, such as $Li_3PO_4$, $LiPO_3$, $LiAlFPO_4$, $LiAl(OH)PO_4$, $LiFePO_4$, $LiMnPO_4$; $Li_2CO_3$; lithium silicates in the form of ladder-type silicates, ino-, phyllo- and tectosilicates, such as $Li_2SiO_3$, $Li_2SiO_4$ and $Li_6Si_2$; lithium sulfates, such as $Li_2SO_4$, $LiHSO_4$, $LiKSO_4$; the Li compounds mentioned during the discussion of the cathode compound, the presence of conductive carbon black being excluded from the mixture when these are used as solid III; and also mixtures of two or more of the Li-ion-conducting solids mentioned above.

Basic solids are particularly suitable here. For the purposes of the invention, basic solids are those whose mixture with a liquid, water-containing diluent, which itself has a pH of not more than 7, has a higher pH than this diluent.

The solids should advantageously be very substantially insoluble in the liquid used as electrolyte, and also be electrochemically inert in the battery medium.

Particularly suitable solids are those which have a primary particle size of from 5 nm to 20 μm, preferably from 0.01 to 10 μm and in particular from 0.1 to 5 μm, the particle sizes given being determined by electron microscopy. The melting point of the solids is preferably above the usual operating temperature of the electrochemical cell, and melting points of above 120° C., in particular above 150° C., have proven particularly advantageous.

The solids here may be symmetrical in their external shape, i.e. have a dimensional ratio of height : width: length (aspect ratio) of about 1 and be shaped as spheres or pellets, be approximately round in shape, or else be in the shape of any desired polyhedron, such as a cuboid, tetrahedron, hexahedron, octahedron or bipyramid, or may be distorted or asymmetric, i.e. have a dimensional ratio of height: width: length (aspect ratio) which is not equal to 1 and be, for example, in the form of needles, asymmetrical tetrahedra, asymmetrical bipyramids, asymmetrical hexa- or octahedra, lamellae or plates, or have fiber-like shape. If the solids are asymmetric particles, the upper limit given above for the primary particle size refers to the smallest axis in each case.

Compounds which may be used as compound VI, which is capable of reacting with a carboxylic acid or sulfonic acid VII or with a derivative or mixture of two or more thereof, are in principle any of the compounds which fulfill this criterion.

Compound VI is preferably selected from the class consisting of: mono- or polyhydric alcohols which have exclusively carbon in their main chain; mono- or polyhydric alcohols which, in their main chain, have, besides at least two carbon atoms, at least one atom selected from the class consisting of oxygen, phosphorus and nitrogen; silicon-containing compounds; amines having at least one primary amino group; amines having at least one secondary amino group; aminoalcohols; mono- or polyfunctional thiols; compounds having at least one thiol and at least one hydroxyl group; and mixtures of two or more of these.

Among these, preference in turn is given to compounds VI which have two or more functional groups able to react with the carboxylic acid or sulfonic acid.

When using compounds VI which contain amino groups as functional group, it is preferable to use those which have secondary amino groups, so that after condensation/crosslinking, mixture 1a contains either no free NH groups at all or only small amounts of such groups.

Individual preferred compounds which may be mentioned are:

- mono- or polyhydric alcohols having exclusively carbon in their main chain and having from 1 to 20 alcoholic OH groups, preferably from 2 to 20 alcoholic OH groups and in particular from 2 to 10 alcoholic OH groups, in particular di-, tri- and tetrahydric alcohols, preferably having from 2 to 20 carbon atoms, such as ethylene glycol, 1,2-propanediol, 1,3-propanediol, 1,2-butanediol, 1,3-butanediol, 1,4-butenediol, 1,4-butynediol, 1,6-hexanediol, neopentyl glycol, 1,2-dodecanediol, glycerol, trimethylolpropane, pentaerythritol, sugar alcohols, hydroquinone, novolak and bisphenol A, but as apparent from the definition above it is also possible to use monohydric alcohols, such as methanol, ethanol, propanol, n-butanol, sec-butanol and tert-butanol; it is moreover also possible to use polyhydroxyolefins, preferably those having two terminal hydroxyl groups, such as α,ω-dihydroxybutadiene;
- polyester polyols, as known, for example, from Ullmann's Encyclopedia of Industrial Chemistry, 4th ed., Vol. 19, pp. 62–65 and obtained, for example, by reacting dihydric alcohols with polybasic, preferably dibasic polycarboxylic acids;
- mono- or polyhydric alcohols which in their main chain contain, besides at least two carbon atoms, at least one oxygen atom, preferably polyetheralcohols, such as polymerization products of alkylene epoxides, for example isobutyleae oxide, propylene oxide, ethylene oxide, 1,2-epoxybutane. 1,2-epoxypentane, 1,2-epoxyhexane, tetrahydrofuran and styrene oxide, use of polyether alcohols modified at the end groups, for example polyether alcohols modified with NH$_2$ end groups, also being possible; these alcohols preferably have a molecular weight (number average) of from 100 to 5000, more preferably from 200 to 1000, and in particular from 300 to 800; compounds of this type are known per se and are commercially available, for example, under the trademarks Pluriol® or Pluronic® (BASF Aktiengesellschaft);
- alcohols as defined above in which some or all of the carbon atoms have been replaced by silicon, in particular polysihoxanes or alkylene oxide/siloxane copolymers or mixtures of polyether alcohols and polysiloxanes. as described, for example, in EP-B 581 296 and EP-A 525 728, where that which has already been said above applies to these alcohols, also with respect to their molecular weight;
- alcohols as defined above, in particular polyether alcohols in which some or all of the oxygen atoms have been replaced by sulfur atoms, where that which has been said above applies likewise to the molecular weight of these alcohols;
- mono- or polyhydric alcohols which contain in their main chain, besides at least two carbon atoms, at least one phosphorus atom or at least one nitrogen atom, for example diethanolamine and triethanolamine; lactones which are derived from compounds of the formula HO—(CH$_2$)$_z$—COOH, where z is a number from 1 to 20, for example ε-caprolactone, β-propiolactone, γ-butyrolactone and methyl-ε-caprolactone;
- silicon-containing compounds, such as di- and trichlorosilane, phenyltrichlorosilane, diphenyldichlorosilane and dimethylvinylchlorosilane; silanols, such as trimethylsilanol;
- amines having at least one primary and/or secondary amino group. for example butylamine, 2-ethylhexylamine, ethylenediamine, hexamethylenediamiue, diethylenetriamine, tetraethylenepentamine, pentaethylenehexamine, aniline and phenylenediamine;
- polyether diamines, such as 4,7-dioxydecane-1,10-diamine and 4,11-dioxytetradecane-1,14-diamine;
- mono- or polyfunctional thiols, such as aliphatic thiols, e.g. methanethiol, ethanethiol, cyclohexanethiol and dodecanetliol; aromatic thiols, e.g. thiophenol, 4-chlorothiophenol and 2-mercaptoaniline;
- compounds having at least one thiol group and at least one hydroxyl group, such as 4-hydroxythiophenol, and also monothio derivatives of the polyhydric alcohols defined above;
- aminoalcohols, such as ethanolamine, N-methylethanolaniine, N-ethylethanolamine, N-butylethanolamine, 2-amino-1-propanol, 2-amino-1-phenyletlianol, and mono- or polyaminopolyols having more than two aliphatically bonded hydroxyl groups, such as tris(hydroxymethyl)-methylamine, glucamine and N,N'-bis(2-hydroxyethyl)ethylenediamine.

It is also possible to use mixtures of two or more of the compounds VI defined above.

According to the invention, the compounds VI mentioned above are condensed with a carboxylic acid or sulfonic acid VII which has at least one functional group capable of free-radical polymerization, or with a derivative thereof or a mixture of two or more thereof, at least one and preferably all of the groups which are free and capable of condensation within the compounds VI being condensed with the compound VII.

For the purposes of the present invention, the carboxylic acid or sulfonic acid VII used may in principle be any carboxylic or sulfonic acid which has at least one functional group capable of free-radical polymerization, or also derivatives of these. The term "derivatives" used here encompasses both compounds which are derived from a carboxylic or sulfonic acid modified at the acid function, such as esters, acid halides and anhydrides, and also compounds which are derived from a carboxylic or sulfonic acid which has been modified on its carbon skeleton, such as halocarboxylic and halosulfonic acids.

Compounds VII which may be mentioned here in particular are:

α,β-unsaturated carboxylic acids and β,γ-unsaturated carboxylic acids.

Particularly suitable α,β-unsaturated carboxylic acids here are those of the formula

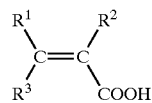

where R$^1$, R$^2$ and R$^3$ are hydrogen or C$_1$–C$_4$-alkyl, and where among these preference is in turn given to acrylic acid and methacrylic acid; successful use may also be made of cinnamic acid, maleic acid, fumaric acid, itaconic acid or p-vinylbenzoic acid, and also derivatives of these, such as anhydrides, e.g. maleic or itaconic anhydride;

halides, in particular chlorides, such as acryloyl or methacryloyl chloride;

esters, such as (cyclo)alkyl (meth)acrylates having up to 20 carbon atoms in the alkyl radical, e.g. methyl, ethyl, propyl, butyl, hexyl, 2-ethylhexyl, stearyl, lauryl, cyclohexyl, benzyl, trifluoromethyl, hexafluoropropyl and tetrafluoropropyl (meth) acrylate, polypropylene glycol mono(meth)acrylates, polyethylene glycol mono(meth)acrylates, poly(meth)acrylates of polyhydric alcohols, for example glycerol di(meth)acrylate, trimethylolpropane di(meth)acrylate, pentaerythritol di- and tri (meth)acrylate, diethylene glycol bis(mono(2-acryloxy)etbyl)carbonate, and poly(meth)acrylates of alcohols which themselves in turn have a group capable of free-radical polymerization, for example esters of (meth)acrylic acid and vinyl and/or allyl alcohol;

vinyl esters of other aliphatic or aromatic carboxylic acids, e.g. vinyl acetate, vinyl propionate, vinyl butyrate, vinyl hexanoate, vinyl octanoate, vinyl decanoate, vinyl stearate, vinyl palirtate, vinyl crotonoate, divinyl adipate, divinyl sebacate, vinyl 2-ethylhexanoate and vinyl trifluoroacetate;

allyl esters of other aliphatic or aromatic carboxylic acids, e.g. allyl acetate, allyl propionate, allyl butyrate, allyl hexanoate, allyl octanoate, allyl decanoate, allyl stearate, allyl palmitate, allyl crotonoate, allyl salicylate, allyl lactate, diallyl oxalate, diallyl malonate, diallyl succinate, diallyl glutarate, diallyl adipate, diallyl pimetate, diallyl cinnamate, diallyl maleate, diallyl phthalate, diallyl isophthalate, triallyl benzene-1,3,5-tricarboxylate, allyl trifluoroacetate, allyl perfluorobutyrate and allyl perfluorooctalioate;

β,γ-unsaturated carboxylic acids or derivatives of these, e.g. vinylacetic acid, 2-methylvinylacetic acid, isobutyl 3-butenoate, allyl 3-butenoate, allyl 2-hydroxy-3-butenoate and diketene;

sulfonic acids such as vinylsulfonic acid, allyl- and methallylsulfonic acid, and also esters and halides of these, vinyl benzenesulfonates and 4-vinylbenzenesulfonamide.

It is also possible to use mixtures of two or more of the carboxylic and/or sulfonic acids described above.

Mention may be made of the following individual compounds X capable of free-radical polymerization and of being used to prepare the polymer IX:

olefinic hydrocarbons, such as ethylene, propylene, butylene, isobutene, hexene and higher homologs, and vinylcyclohexane;

(meth)acrylonitrile;

halogen-containing olefinic compounds, such as vinylidene fluoride, vinylidene chloride, vinyl fluoride, vinyl chloride, hexafluoropropene, trifluoropropene, 1,2-dichloroethylene, 1,2-difluoroethylene and tetrafluoroethylene;

vinyl alcohol, vinyl acetate, N-vinylpyrrolidone, N-vinylimidazole and vinylformamide;

phosphorus nitrile chlorides, such as phosphonitrile dichloride and hexachlorotriphosphazene, and also derivatives of these substituted to some extent or fully by alkoxy, phenoxy, amino or fluoroalkoxy, i.e. compounds which can be polymerized to give polyphosphazenes;

aromatic olefinic compounds, such as styrene and α-methylstyrene;

vinyl ethers, such as methyl, ethyl, propyl, isopropyl, butyl, isobutyl, hexyl, octyl, decyl, dodecyl, 2-etbylhexyl, cyclohexyl, benzyl, trifluoromethyl, hexafluoropropyl and tetrafluoropropyl vinyl ether.

It is, of course also possible to use mixtures of the above compounds X, this then giving rise to copolymers which, depending on the preparation method, contain the monomers in random distribution or are formed as block copolymers.

These compounds X, like the condensation products V, are polymerized in the conventional way well known to the person skilled in the art, preferably by free-radical polymerization; in relation to the molecular weights obtained that which is said in the text below concerning compound VIII is applicable.

Compounds VIII are mainly compounds with an average molecular weight (number average) of at least 5000, preferably from 5000 to 20,000,000, in particular from 100,000 to 6,000,000, and capable of solvating lithium cations and of functioning as a binder. Examples of suitable compounds VIII are polyethers and copolymers which have at least 30% by weight, based on the total weight of compound VIII, of the following structural unit:

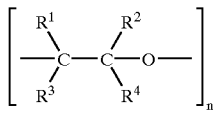

where $R^1$, $R^2$, $R^3$ and $R^4$ are aryl or alkyl, preferably methyl, or hydrogen, and may be identical or different, and may contain heteroatoms, such as oxygen, nitrogen, sulfur or silicon.

Compounds this type are described, for example, in: M. B. Armand et al., Past Ion Transport in Solids, Elsevier, N.Y., 1979, pp. 131–136, and in FR-A 7832976.

Compound VIII may also be composed of mixtures of two or more compounds of this type.

The polymer composition IV defined above and/or the polymer IX may also be a foam, the solid II then being distributed as such therein.

According to the invention, the mixes IIa should be composed of from 1 to 95% by weight, preferably from 25 to 90% by weight and in particular from 30 to 70% by weight, of a solid III and of from 5 to 99% by weight, preferably from 10 to 75% by weight and in particular from 30 to 70% by weight, of a polymeric composition IV, where the compound VIII in the polymeric composition IV should advantageously have an average molecular weight (number average) of from 5000 to 100,000,000, preferably from 50,000 to 8,000,000. The polymeric composition IV may be obtained by reacting from 5 to 100% by weight, preferably from 30 to 70% by weight, based on the polymeric composition IV, of a compound V and from 0 to 95% by weight, in particular from 30 to 70% by weight, based on the polymeric composition IV, of a compound VIII.

According to the invention, the mixes IIb should be composed of from 1 to 95% by weight, preferably from 25 to 90% by weight, and in particular from 30 to 70% by weight, of a solid III and of from 5 to 99% by weight, preferably from 10 to 75% by weight and in particular from 30 to 70% by weight, of a polymer IX, where the compound VIII in the polymer IX advantageously has an average molecular weight (number average) of from 5000 to 100,000,000, preferably from 50,000 to 8,000,000. The polymer IX may be obtained by reacting from 5 to 75% by weight, preferably from 30 to 70% by weight, based on the polymer IX, of a compound X and from 25 to 95% by weight in particular from 30 to 70% by weight, based on the polymer IX, of a compound VIII.

The novel mixture also contains at least one ester of the formulae (E1) to (E5) as defined at the outset.

Among the esters mentioned above of the formulae (E1) to (E5), preference is given to the use of the phosphates of the formula (E3).

Examples of groups $R^1$ and $R^2$ and, if present, $R^3$ and/or $R^4$ are methyl, ethyl, n-propyl, isopropyl, n-butyl, tert-butyl, cyclopentyl, cyclohexyl and benzyl, and also (—$CH_2$—$CH_2$—$O)_n$—$CH_3$ where n is from 1 to 3, care being taken as mentioned above however that at least one of the groups $R^1$, $R^2$, $R^3$ or $R^4$ is (—$CH_2$—$CH_2$—$O)_n$—$CH_{13}$, where n is from 1 to 3, preferably 1 or 2.

It is also preferable to use esters of the formulae (E1) to (E5) in which $R^1$, $R^2$ and, if present, $R^3$ and/or $R^4$ are identical and are —$CH_2$—$CH_2O$—$CH_3$ or (—$CH_2$—$CH_2$—$O)_2$—$CH_3$, the corresponding phosphates being preferred here once again.

Examples of compounds whose use is particularly preferred are those of the formulae (E1a) to (E5a):

(E1a)

(E2a)

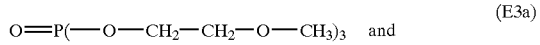
(E3a)

(E4a)

(E5a)

Because of their properties, the esters used here are exceptionally suitable as plasticizers in mixtures according to the invention, and generally have a viscosity at room temperature of $\leq 10$ mPas, preferably $\leq 5$ mPas and in particular $\leq 3$ mPas. They generally have boiling points of about 200° C. or above, preferably about 250° C. or above, and in particular about 300° C. or above, measured in each case at atmospheric pressure, and have a sufficiently low vapor pressure of from about $10^{-5}$ to about 10 mbar at the temperatures of from about −50° C. to about 150° C. at which they are used. Their high boiling points mean that they can be distilled and can therefore be prepared with high purity. These esters are, furthermore, liquid at atmospheric pressure over a wide temperature range, generally remaining liquid down to about −30° C., preferably down to about −40° C. The esters described for this purpose may be used as solvents in electrolyte systems for Li-ion storage batteries at at least about 80° C., preferably at at least about 120° C., and more preferably at at least about 150° C.

It is, of course, also possible to use the esters used according to the invention as mixtures with the plasticizers mentioned below.

Preference is given to solvent combinations which have sufficiently low viscosity, are capable of powerful solvation of the ions of the conducting salts, are liquid over a wide temperature range and are adequately electrochemically and chemically stable and resistant to hydrolysis.

The content of the esters in the novel mixture is generally from 1 to 200% by weight, preferably from 2 to 100% by weight and more preferably from 2 to 70% by weight, based in each case on the mix IIa/IIb.

The esters used according to the invention are prepared by conventional processes, as described, for example, by K. Mura Kami in Chem. High Polymers (Japan), 7, pp. 188–193 (1950) and in H. Steinberg, Organoboron Chemistry, Chapter 5, J. Wiley & Sons, N.Y., 1964. The starting materials here are generally the acids, anhydrides or acid chlorides on which the esters are based, for example boric acid, $C(O)Cl_2$, $POCl_3$, $SO_2Cl_2$ and $SiCl_4$, and these are reacted in a known manner with the corresponding mono- or polyhydric alcohols or etherols.

The novel mixtures Ia and Ib and the mixes IIa and IIb are discussed together below and are termed, respectively, "novel mixture" and "novel mix".

The novel mixture comprises the novel mix and the ester in amounts of from 1 to 100% by weight, preferably from 35 to 100% by weight, based in each case on the novel mixture. To prepare the same, use may be made of a mix made from: a solid III, a condensation product V and, if desired, a compound VIII, or of a mix made from: a solid III, a compound X, a compound VIII, and at least one ester of the formula (E1) to (E5), as well as, if desired, of usual additives, such as other plasticizers, preferably those comprising polyethylene oxide or polypropylene oxide.

Other plasticizers used may be aprotic solvents, preferably those which solvate Li ions, for example dimethyl carbonate, diethyl carbonate, dipropyl carbonate, diisopropyl carbonate, dibutyl carbonate, ethylene carbonate and propylene carbonate; oligoalkylene oxides, such as dibutyl ether, di-tert-butyl ether, dipentyl ether, dihexyl ether, diheptyl ether, dioctyl ether, dinonyl ether, didecyl ether, didodecyl ether, ethylene glycol dimethyl ether, ethylene glycol diethyl ether, 1-tert-butoxy-2-methoxyethane, 1-tert-butoxy-2-ethoxyethane, 1,2-dimethoxypropane, 2-methoxyethyl ether, 2-ethoxyetliyl ether, diethylene glycol dibutyl ether, dimetylene glycol tert-butyl methyl ether, triethylene glycol dimethyl ether, tetraethylene glycol dimethyl ether, γ-butyrolactone and dimethylformamide; hydrocarbons of the formula $C_nH_{2n+2}$ where $7<n<50$; organic phosphorus compounds, in particular phosphates and phosphonates, such as trimethyl phosphate, triethyl phosphate, tripropyl phosphate, tributyl phosphate, triisobutyl phosphate, tripentyl phosphate, trihexyl phosphate, trioctyl phosphate, tris(2-ethylhexyl) phosphate, tridecyl phosphate, diethyl n-butyl phosphate, tris(butoxyethyl) phosphate, tris(2-methoxyethyl) phosphate, tris(tetrahydrofuryl) phosphate, tris(1H,1H,5H-octafluoropentyl) phosphate, tris(1H,1H-trifluoroetlyl) phosphate, tris(2-(diethylamino)ethyl) phosphate, diethyl ethylphosphonate, dipropyl propylphosphonate, dibutyl butylphosphonate, dihexyl hexylphospbonate, dioctyl octylphosphonate, ethyl dimethylphosphonoacetate, methyl diethylphosphonoacetate, triethyl phosphonoacetate, dimethyl 2-oxopropylphosphonate, diethyl 2-oxopropylphosphonate, dipropyl 2-oxopropylphosphonate, ethyl diethoxyphosphinylformate, trimethyl phosphonoacetate, triethyl phosphonoacetate, tripropyl phosphonoacetate and tributyl phosphonoacetate; organic sulfur compounds, such as sulfates, sulfonates, sulfoxides, sulfones and sulfites, for example dimethyl sulfite, diethyl sulfite, glycol sulfite, dimethyl sulfone, diethyl sulfone, diethylpropyl sulfone, dibutyl sulfone, tetramethylene sulfone, methylsulfolane, dimethyl sulfoxide, diethyl sulfoxide, dipropyl sulfoxide, dibutyl sulfoxide, tetramethylene sulfoxide, ethyl methanesulfonate, 1,4-butanediol bis(methanesulfonate), diethyl sulfate, dipropyl sulfate, dibutyl sulfate, dihexyl sulfate, dioctyl sulfate and $SO_2ClF$; and nitriles, such as acrylonitrile;

dispersants, in particular those with surfactant structure;
and mixtures of these.

The mixtures according to the invention may be dispersed or dissolved in an inorganic or preferably an organic liquid diluent, where the mixture according to the invention should have a viscosity of preferably from 100 to 50,000 mPas, and may then be applied in a manner known per se, such as spray coating, casting, dipping, spin coating, roller coating, relief printing, gravure printing or planography or screen printing onto a carrier material. Further processing can take place in the usual way, e.g. by removing the diluent and curing the mixture.

Suitable organic diluents are aliphatic ethers, in particular tetrahydrofuran and dioxane, hydrocarbons, in particular hydrocarbon mixtures such as petroleum spirit, toluene and xylene, aliphatic esters, in particular ethyl acetate and butyl acetate, and ketones, in particular acetone, ethyl methyl ketone and cyclohexanone. It is also possible to use combinations of diluents of this type.

Carrier materials which may be used are those usually used for electrodes, preferably metals, such as aluminum and copper. It is also possible to use temporary carriers, such as films, in particular polyester films, such as polyethylene terephthalate films. Such films may advantageously be provided with a release layer, preferably of polysiloxanes.

The solid electrolytes and separators may likewise be produced thermoplastically from the mixture according to the invention, for example by injection molding, melt casting, compression molding, kneading or extrusion, if desired followed by a calendering step.

After the mixture according to the invention has formed a film, volatile components, such as solvents or plasticizers. may be removed.

The crosslinking of the mixture according to the invention may be done in a manner known per se, for example by irradiating with ionic or ionizing radiation, or an electron beam, preferably with an acceleration voltage of from 20 to 2000 kV and a radiation dose of from 5 to 50 Mrad, or UV or visible light, and it is usually advantageous here to add an initiator, such as benzil dimethyl ketal or 1,3,5-trimethylberzoyltriphenylphosphine oxide in amounts of in particular at most 1% by weight, based on the polymeric composition IV and the polymer IX, respectively, and the crosslinking may generally be carried out within from 0.5 to 15 minutes, advantageously under an inert gas, such as nitrogen or argon; by thermal free-radical polymerization, preferably at temperatures above 60° C., it being possible and advantageous to add an initiator, such as azobisisobutyronitrile, generally in amounts of at most 5% by weight, preferably from 0.05 to 1% by weight, based on the polymeric composition IV and the polymer IX, respectively; by electrochemically induced polymerization; or by ionic polymerization, for example by acid-catalyzed cationic polymerization, possible catalysts being primarily acids, preferably Lewis acids, such as $BF_3$ or in particular $LiBF_4$ or $LiPF_6$. Lithium-ion-containing catalysts, for example $LiBF_4$ or $LiPF_6$, here may advantageously remain as conducting salt in the solid electrolyte or separator.

If the mixture according to the invention is to be used as a solid electrolyte or a separator in an electrochemical cell, a dissociable compound containing lithium cations, known as a conducting salt, and other additives if desired, such as in particular organic solvents, known as an electrolyte, may be incorporated.

The addition of these materials to the mixture may take place to some extent or completely during the production of the layer, or they may be introduced into the layer after it has been produced.

The conducting salts which may be used are those which are well known and described, for example, in EP-A 0 096 629. It is preferable according to the invention for the conducting salt used to be $LiPF_6$, $LiBF_4$, $LiClO_4$, $LiAsF_6$, $LiCF_3SO_3$, $LiC(CF_3SO_2)_3$, $LiN(CF_3SO_2)_2$, $Li(C_nF_{2n+1})SO_3$, $LiC[(C_nF_{2n+1})SO_2]_3$, $LiN(C_nF_{2n+1}SO_2)_2$, where n is from 2 to 20, $LiN(SO_2F)_2$, $LiAlCl_4$, $LiSiF_6$, $LiSbF_6$ or a mixture of two or more of these, use of $LiBF_4$ as conducting salt being preferred. Particular preference is given to the combination of the esters of the formulae (E1a) to (E5a) with $LiBF_4$ as conducting salt, and particular preference is given to the combination of the ester of the formula (E3a) with $LiBF_4$ as conducting salt.

Possible electrolytes, besides the esters present in the mixture, are the compounds discussed above under "plasticizers", preference being given to the use of the usual organic electrolytes, preferably esters, such as ethylene carbonate, propylene carbonate, dimethyl carbonate and diethyl carbonate or mixtures of compounds of this type.

The novel solid electrolytes, separators and/or electrodes suitable for electrochemical cells should advantageously have a thickness of from 5 to 500 $\mu$m, preferably from 10 co 500 $\mu$m. more preferably from 10 to 200 $\mu$m and in particular from 20 to 100 $\mu$m.

If the novel mixture is to be used as, or for preparing, a cathode, then one of the conventionally used electron-conducting, electrochemically active compounds (cathode compound) is incorporated, preferably a lithium compound. Particular examples of these are:

$LiCoO_2$, $LiNiO_2$, $LiNi_xCo_yO_2$, $LiNi_xCo_yAl_zO_2$, where $0<x,y,z\leq 1$, $Li_xMnO_2$ ($0<x\leq 1$), $Li_xMn_2O_4$ ($0<x\leq 2$), $Li_xMoO_2$ ($0<x\leq 2$), $Li_xMnO_3$ ($0<x\leq 1$), $Li_xMnO_2$ ($0<x\leq 2$), $Li_xMn_2O_4$ ($0<x\leq 2$), $Li_xV_2O_4$ ($0<x\leq 2.5$), $Li_xV_2O_3$ ($0<x\leq 3.5$), $Li_xVO_2$ ($0<x\leq 1$), $Li_xWO_2$ ($0<x\leq 1$), $Li_xWO_3$ ($0<x\leq 1$), $Li_{xTiO2}$ ($0<x\leq 1$), $Li_xTi_2O_4$ ($0<x\leq 2$), $Li_xRuO_2$ ($0<x\leq 1$), $Li_xFe_2O_3$ ($0<x\leq 2$), $Li_xFe_3O_4$ ($0<x\leq 2$), $Li_xCr_2O_3$ ($0<x\leq 3$), $Li_xCr_3O_4$ ($0<x\leq 3.8$), $Li_xV_3S_5$ ($0<x\leq 1.8$), $Li_xTa_2S_2$ ($0<x\leq 1$), $Li_xFeS$ ($0<x\leq 1$), $Li_xFeS_2$ ($0<x\leq 1$), $Li_xNbS_2$ ($0<x\leq 2.4$), $Li_xMoS_2$ ($0<\leq 3$), $Li_xTiS_2$ ($0<x\leq 2$), $Li_xZrS_2$ ($0<x\leq 2$) $Li_xNbSe_2$ ($0<x\leq 3$), $Li_xVSe_2$ ($0<x\leq 1$), $Li_xNiPS_2$ ($0<x\leq 1.5$), $Li_xFePS_2$ ($0<x\leq 1.5$).

For use as an anode, the anode material incorporated is a conventional electron-conducting, electrochemically active compound (anode compound) known from the prior art, of which the following in particular may be mentioned:

lithium, lithium-containing metallic alloys, micronized carbon black, natural and synthetic graphite, synthetically graphitized carbon dust and carbon fibers, oxides, such as titanium dioxide, zinc oxide, tin oxide, molybdenum oxide and tungsten oxide, and carbonates, such as titanium carbonate, molybdenum carbonate and zinc carbonate.

When the novel mixture is used as, or for producing, an anode, it contains an addition of up to 20% by weight, based on the total weight of the mixture, of conductivity black and, if desired, the usual additives mentioned above. If the mixture is used as, or for producing. a cathode, it contains, based on its total weight, from 0.1 to 20% by weight of conductivity black.

The novel mixtures may be used in electrochemical cells as sole solid electrolyte and/or separator and/or electrode, or in a mixture with other solid electrolytes, separators and/or electrodes.

The present invention moreover provides a composite which can be used in particular in electrochemical cells, preferably in the form of a film, more preferably in the form of a film with an overall thickness of from 15 to 1500 $\mu$m, in particular with an overall thickness of from 50 to 500 $\mu$m, encompassing at least one first layer which comprises an electron-conducting, electrochemically active compound, and at least one second layer which comprises the novel mixture defined above and is free from electron-conducting, electrochemically active compounds.

The present invention also describes a process encompassing the following stages for producing a composite of this type:

(I) producing at least one first layer, as defined above;
(II) producing at least one second layer, as defined above; and
(III) then bringing together the at least one first layer with the at least one second layer by means of a conventional process for providing layers.

It is preferable to produce the at least one second layer on a temporary carrier. According to the invention, use may be made here of conventionally used temporary carriers, such as a release film made from a polymer or from a preferably coated paper, e.g. a siliconized polyester film. It is, however, also possible to produce this second layer on a permanent carrier, such as a collector electrode, or else even entirely without a carrier.

The bringing together and the production of the layers defined above takes place by means of atmnospheric-pressure processes for providing layers or for the production of films, such as casting or doctoring, or also by process methods at superatmospheric pressure, such as extrusion, lamination, calendering or compression molding. The composite thus produced may, if desired, be crosslinked and/or hardened by radiation, electrochemically or thermally.

Besides the second layer defined above, the first layer defined above may, of course, also comprise the novel mixture.

As apparent from the above, this method makes it possible with ease to provide a composite with the constituents release film/separator (second layer)/electrode (first layer).

It is also possible, by double-sided coating, to provide a composite with the constituents anode/sepa-rator/cathode.

An example of a procedure for this is:

Anode materials, e.g. tin oxide, conductivity black, the novel mixture, a conducting salt and a plasticizer, e.g. propylene carbonate, are firstly mixed with one another and the resultant blend is cast onto a collector electrode and then irradiated with UV light (component 1). A cathode material, e.g. $LiMn_2O_4$, is then applied to a collector electrode coated with conductivity black, and onto this is cast a blend of the novel mixture, a conducting salt and a plasticizer. This composite, too, is then UV-irradiated (component 2). Bringing together the two components described above gives a composite which, combined with any desired solid and/or liquid electrolyte, can be used as an electrochemical cell.

It is also possible to produce an anode/separator/cathode composite as described above even without using a carrier and/or the collector electrodes, since the resultant composite composed of a first and a second layer, as defined above, has sufficient mechanical stability in its own right for use in electrochemical cells.

The filling of composites of this type with an electrolyte and conducting salt may take place either before the layers are brought together or else, preferably, after they are brought together, if desired after contact has been established with suitable collector electrodes, e.g. with a metal film, and can even take place after the composite has been introduced into a battery casing; die specific microporous structure of the layers when the mixture according to the invention is used, resulting in particular from the presence of the solid defined above in the separator and, if present, in the electrodes, makes it possible for the electrolyte and the conducting salt to be absorbed and the air in the pores to be displaced. The filling may be carried out at from 0 to about 100° C., depending on the electrolyte used.

The novel electrochemical cells may be used in particular as automobile battery, appliance battery, flat-type battery or all-plastics battery.

As apparent from the above, the present invention also provides the use of the novel mixture or of the composite described above for producing a solid electrolyte, a separator or an electrode, or in a sensor, in an electrochromic window, in a display, in a capacitor or in an ion-conducting film; it also provides a solid electrolyte, a separator, an electrode, a sensor, an electro-chromic window, a display, a capacitor and an ion-conducting film, each of which comprise the novel mixture or the composite described above.

The invention further provides an electrochemical cell encompassing a solid electrolyte, a separator or an electrode, as defined above, or a combination of two or more of these, and also the use of the electrochemical cell defined above as an automobile battery, appliance battery or flat-type battery.

EXAMPLES

Example of Preparation of an Ester

To prepare the phosphates of the formula $O=P(-O-CH_2-CH_2-OCH_3)_3$, 274 g (3.6 mol) of methylglycol were placed in a 1000 ml round-bottomed flask with 2 g of $ZnCl_2$ and cooled to 5° C. 153.33 g (1 mol) of $POCl_3$ were then added dropwise within a period of 50 min, the temperature being held at from about 5 to 10° C. After the addition had finished, the solution was clear and was allowed to warm to room temperature. The resultant product mixture was then distilled under reduced pressure (from 80 to 90 mbar) at from about 50 to 55° C. in order to remove unreacted starting material and by-products.

A further distillation was then carried out at very low pressure (about 0.02 mbar) at about 170° C., giving the desired product. The water content of the above phosphate was 20 ppm.

Example 1

75 g of a wollastonite (Tremin® 800 EST, Quarzwerke Frechen) which had an average particle size of 3 $\mu$m and had been hydrophobicized with epoxysilane and whose aqueous suspension had a pH of 8.5, was dispersed by a high-speed stirrer in 300 g of toluene and 5 g of the phosphate of the preparative example. The following were then added to the mixture: 12.5 g of a polyethylene oxide having an average molecular weight (number average) of 2,000,000 (Polyox®, Union Carbide), 12.5 g of a dimethacrylate of a propylene oxide-ethylene oxide block polymer (Pluriol® PE600, BASF Aktiengesellschaft) and 0.02 g of a UV photoinitiator (Lucirin® BDK, BASF Aktieugesellschaft).

The mixture was then applied, using a doctor with a coating gap of 300 $\mu$m, to a siliconized release paper at 60° C., the diluent was removed within a period of 5 minutes, and peeling of the dried coating gave a film of about 40 $\mu$m thickness which was photo-crosslinked under an argon atmosphere by irradiation for 10 minutes at a distance of 5 cm in a field of superactinic fluorescent tubes (TL 09, Philips).

The flexible film had excellent flexural strength, and tolerated bending radii down to well below 1 mm without fracturing.

The film also showed no spherulite-type polyethylene oxide crystals after storage for two weeks at room temperature, and had good resistance to swelling in the organic electrolytes which have been mentioned and which contain a conducting salt.

The organic electrolytes containing a conducting salt were absorbed in sufficient amounts within a few minutes through a process of spontaneous diffusion into the material, with swelling, in weight terms, of less than 50% by weight.

The swollen film had good strength.

Comparative Example 1

12.5 g of a polyethylene oxide having an average molecular weight (number average) of 2,000,000 (Polyox®, Union Carbide), 12.5 g of a dimethacrylate of a propylene oxide-ethylene oxide block polymer (Pluriol® PE600, BASF Aktiengesellschaft) and 0.02 g of a UW photoinitiator (Lucirin® BDK, BASF Aktiengesellschaft) were dissolved in 200 g of THF.

The mixture was then applied, using a doctor with a coating gap of 750 μm, to a siliconized release paper at 60° C., the diluent was removed within a period of 5 minutes. and peeling off the dried coating gave a film of about 40 μm thickness which was photo-crosslinked under an argon atmosphere by irradiation for 10 minutes at a distance of 5 cm in a field of superactinic fluorescent tubes (TL 09, Philips).

The flexible film had excellent flexural strength, and tolerated bending radii down to well below 1 mm without fracturing. The film also showed no spherulite-type polyethylene oxide crystals after storage for two weeks at room temperature, and had satisfactory resistance to swelling in the organic electrolytes which have been mentioned and which contain a conducting salt.

The organic electrolytes containing a conducting salt were absorbed in sufficient amounts within a few minutes through a process of spontaneous diffusion into the material, with swelling, in weight terms, of less than 150% by weight, with considerable change taking place in the size and thickness of the film.

Its strength was markedly lower than was the case in Example 1.

In lithium-ion batteries, the film always caused failure of the cells as a result of excessive self-discharge rates or micro short-circuits.

The results are given in the table.

Comparative Example 2

75 g of a wollastonite (Tremim® 800 EST, Quarzwerke Prechen) which had an average particle size of 3 μm and had been hydrophobicized with epoxysilane and whose aqueous suspension had a pH of 8.5, was dispersed by a high-speed stirrer in 300 g of toluene. The following were then added to the mixture 12.5 g of a polyethylene oxide having an average molecular weight (number average) of 2,000,000 (Polyox®, Union Carbide), 12.5 g of a dirnethacrylate of a propylene oxide-ethylene oxide block polymer (Pluriol® PE600, BASF Aktiengesellschaft) and 0.02 g of a TV photoinitiator (Lucirin® BDK, BASF Aktiengesellschaft).

The mixture was then applied, using a doctor with a coating gap of 300 μm, to a siliconized release paper at 60° C., the diluent was removed within a period of 5 minutes, and peeling off the dried coating gave a film of about 40 μm thickness.

The flexible film had excellent flexural strength, and tolerated bending radii down to well below 1 mm without fracturing.

The film also showed no spherulite-type polyethylene oxide crystals after storage for two weeks at room temperature, and had insufficient resistance to swelling in the organic electrolytes which have been mentioned and which contain a conducting salt. Even after a few minutes of swelling time, fissures appear or the film sticks to itself, so that the swollen film is no longer handleable.

The results are given in the table.

Comparative Example 3

As in U.S. Pat. No. 5,429,891, Example 1 (F), to a mixture of 30 g of a vinylidene fluoride hexafluoropropene copolymer (Kynarflex® 2822, Elf Atochem), 20 g of a silanized pyrogenic silica (Aerosil R974, Degussa) whose aqueous suspension has a pH of 7,50 g of dibutyl phthalate (Palatinol C, BASF Aktiengesellschaft) and 200 g of acetone were added 5% by weight, based on dibutyl phthalate, on trimethylolpropane trimethacrylate.

The mixture was then applied to a glass plate using a doctor with a coating gap of 750 μm, dried in a stream of air for 15 minutes, and embedded between layers of Mylar® of thickness 0.075 mm. The film layer of thickness 100 μm was then crosslinked by irradiation with electrons of an energy level of 4.5 MeV, at a dose of 5 Mrad, a dose of 2.5 Mrad being used for each pass.

The flexible film bad good flexural strength.

Before use of the film in lithium-ion batteries, it was necessary for complicated measures to be taken to remove the plasticizer by extraction from the film, since otherwise the cycle stability achieved was inadequate due to poisoning of the electrodes. To remove the plasticizer, the film was extracted five times, for 10 minutes on each occasion, with 50 times its own weight of diethyl ether at room temperature. After the plasticizer has been removed, the film is unstable and easily fractures on bending.

The plasticizer-free film showed good resistance to swelling in the organic electrolytes which have been mentioned and which contain a conducting salt.

The organic electrolytes containing a conducting salt were absorbed in sufficient amounts within a few minutes by spontaneous diffusion into the material.

The swollen film had good strength.

The results are given in the table below.

TABLE

|  | Ex. 1 | Comp. 1 | Comp. 2 | Comp. 3 |
|---|---|---|---|---|
| Strength with plasticizer | not applicable | not applicable | not applicable | 2 |
| Extraction | not applicable | not applicable | not applicable | required |
| Strength without plasticizer | 2 | 2 | 5 | 5 |
| Resistance to swelling | 2 | 3 | 5 | 2 |
| Strength after swelling | 2 | 4 | 6 | 2 |
| Conductivity | 2 | 2 | 4 | 2 |
| Short-circuit protection | 1 | 4 | 6 | 1 |
| Current capacity | 1 | 5 | 6 | 4 |
| Cycle stability | 1 | 5 | 6 | 2 |

Grades:
1 very good
2 good
3 satisfactory
4 unsatisfactory
5 poor
6 so poor that test could not be carried out

We claim:

1. A mixture Ia, comprising a mix IIa composed of
   a) from 1 to 95% by weight of a solid III with a primary particle size of from 5 nm to 20 μm and
   b) from 5 to 99% by weight of a polymeric composition IV, obtained by polymerizing
      b1) from 5 to 100% by weight, based on the composition IV, of a condensation product V of
         α) at least one compound VI which is capable of reacting with a carboxylic acid or with a sulfonic acid or with a derivative or a mixture of two or more of these, and
         β) at least 1 mol per mole of the compound VI of a carboxylic acid or sulfonic acid VII which has at least one functional group capable of free-radical polymerization, or of a derivative thereof or of a mixture of two or more thereof and
      b2) from 0 to 95% by weight, based on the composition IV, of another compound VIII with an average molecular weight (number average) of at least 5000 having polyether segments in its main or side chain and at least one ester of the formula (E1) to (E4) as a component c)

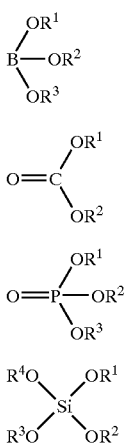

(E1)
(E2)
(E3)
(E4)

where each of $R^1$, $R^2$, $R^3$ and $R^4$ is identical with or different from the others and, independently of the others, is linear or branched-chain $C_1$-$C_4$-alkyl, $(-CH_2-CH_2-O)_n-CH_3$, where n is from 1 to 3, $C_3$-$C_6$-cycloalkyl or an aromatic hydrocarbon group, which may in turn be substituted, with the proviso that at least one of the groups $R^1$, $R^2$, $R^3$ or $R^4$ is $(-CH_2-CH_2-O)_n-CH_3$, where n is from 1 to 3.

2. A mixture Ib, comprising a mix IIb composed of
   a) from 1 to 95% by weight of a solid III with a primary particle size of from 5 nm to 20 μm and
   b) from 5 to 99% by weight of a polymer IX, obtained by polymerizing
      b1) from 5 to 75% by weight, based on the polymer IX, of a compound X capable of free-radical polymerization and differing from the carboxylic acid or the sulfonic acid VII or from a derivative thereof, or of a mixture of two or more thereof and
      b2) from 25 to 95% by weight, based on the polymer IX, of another compound VII with an average molecular weight (number average) of at least 5000, having polyether segments in its main or side chain, and at least one ester of the formula (E1) to (E4) as a component c)

 (E1)

 (E2)

 (E3)

 (E4)

where each of $R^1$, R $R^3$ and $R^4$ is identical with or different from the others and, independently of the others, is, linear or branched-chain $C_1$-$C_4$-alkyl, $(-CH_2-CH_2-O)_n-CH_3$, where n is from 1 to 3, $C_{3-C6}$-cycloalkyl or an aromatic hydrocarbon group, which may in turn be substituted, with the proviso that at least one of the groups $R^1$, $R^2$, $R^3$ or $R^4$ is $(-CH_2-CH_2-O)_n-CH_3$, where n is from 1 to 3.

3. A mixture as claimed in claim 1, where in the at least one ester of the formula (E1) to (E4) $R^1$, $R^2$ and, if present $R^3$ and/or $R^4$ are identical and are $-CH_2-CH_2-O-CH_3$ or $(-CH_2-CH_2-_O)_2-CH_3$.

4. A mixture as claimed in claim 2 where in the at least one ester of the formula (E1) to (E4) $R^1$, $R^2$ and, if present, $R^3$ and/or $R^4$ are identical and are $-CH_2-CH_2-O-CH_3$ or $(-CH_2-CH_2-O)_2-CH_3$.

5. A mixture as claimed in claim 1, where the at least one ester is selected from the class consisting of compounds (E1a) to (E4a):

 (E1a)

 (E2a)

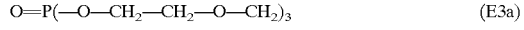 (E3a)

and

 (E4)

6. A mixture as claimed in claim 2, where the at least one ester is selected from the class consisting of compounds (E1a) to (E4a):

 (E1a)

 (E2a)

 (E3a)

and

 (E4a)

7. A mixture as claimed in claim 1 where the mix IIa is composed of
   a) from 1 to 95% by weight of a solid III with a primary particle size of 5 nm to 20 μm and
   b) from 5 to 99% by weight of a polymeric composition IV, obtained by polymerizing
      b1) from 5 to 100% by weight, based on the composition IV, of a condensation product V of α) a polyhydric alcohol VI containing carbon and oxygen in its main chain and β) at least one mol per mole of polyhydric alcohol VI of an α,β-unsaturated carboxylic acid VII and b2) from 0 to 95% by weight, based on the composition IV, of another compound VIII with an average molecular weight (number average) of at least 5000, having polyether segments in its main or side chain.

8. A mixture as claimed in claim 1, further containing at least one conducting salt selected from the class consisting of $LiPF_6$, $LiBF_4$, $LiClO_4$, $LiAsF_6$, $LiCF_3SO_3$, $LiC(CF_3SO_2)_3$, $LiN(CF_3SO_2)_2$, $LiN(LiN(SO_2F)_2$, $LiN(CF_3CF_3SO_2)_2$, $LiAlCl_4$, $LiSiF_6$ and $LiSbF_6$.

9. A mixture as claimed in claim 2, further containing at least one conducting salt selected from the class consisting of $LiPF_6$, $LiBF_4$, $LiClO_4$, $LiAsF_6$, $LiCF_3SO_3$, $LiC(CF_3SO_2)_3$, $LiN(CF_3SO_2)_2$, $LiN(LiN(SO_2F)_2$, $LiN(CF_3CF_3SO_2)_2$, $LiAlCl_4$, $LiSiF_6$ and $LiSbF_6$.

10. A mixture as claimed in claim 8, containing at least one compound (E1a) to (E4a) and $LiBF_4$.

11. A mixture as claimed in claim 9, containing at least one compound (E1a) to (E4a) and $LiBF_4$.

12. A composite encompassing at least one first layer which comprises an electron-conducting, electrochemically active compound, and at least one second layer which comprises a mixture as claimed in claim 11 and is free from electron-conducting, electrochemically active compounds.

13. A composite encompassing at least one first layer which comprises an electron-conducting, electrochemically active compound, and at least one second layer which comprises a mixture as claimed in claim 2 and is free from electron-conducting, electrochemically active compounds.

14. A mixture as claimed in claim 1, where solid III is basic.

15. A mixture as claimed in claim 2, where solid III is basic.

16. A mixture as claimed in claim 7, where solid III is basic.

17. A mixture as claimed in claim 1, wherein the content of component c) is from 1 to 200% by weight, preferably from 2 to 100% by weight, more preferably 2 to 70% by weight, based in, each case on the mix IIa.

18. A mixture as claimed in claim 2, wherein the content of component c) is from 1 to 200% by weight, preferably from 2 to 100% by weight, more preferably from 2 to 70% by weight, based in each case on the mix IIb.

* * * * *

UNITED STATES PATENT AND TRADEMARK OFFICE
CERTIFICATE OF CORRECTION

PATENT NO. : 6,642,294 B1
DATED : November 4, 2003
INVENTOR(S) : Bauer et al.

It is certified that error appears in the above-identified patent and that said Letters Patent is hereby corrected as shown below:

Title page,
Item [30], Foreign Application Priority Data, delete the following erroneously listed priority application: "Apr. 13, 1999    (DE) ……………….. 199 16 562".
Item [57], ABSTRACT,
Line 11, "iixture" should be -- mixture --.

Column 20,
Line 24, "$C_{3\text{-}C6}$" should be -- $C_3$-$C_6$- --;
Line 31, "$(\text{-}CH_2\text{-}CH_{2\text{-}O})_2\text{-}CH_3$" should be -- $(\text{-}CH_2\text{-}CH_2\text{-}O)_2\text{-}CH_3$ --.
Line 43, "$O=P(\text{-}O\text{-}CH_2\text{-}O\text{-}CH_3)_3$" should be -- $O=P(\text{-}O\text{-}CH_2\text{-}CH_2\text{-}O\text{-}CH_3)_3$ --.

Column 21,
Lines 12 and 17, "$LiN(LiN(SO_2F)_2$" should be -- $LiN(SO_2F)_2$ --.

Signed and Sealed this

Tenth Day of February, 2004

JON W. DUDAS
*Acting Director of the United States Patent and Trademark Office*